United States Patent [19]

Dexter et al.

[11] 4,226,763

[45] Oct. 7, 1980

[54] 2-[2-HYDROXY-3,5-DI-($\alpha,\alpha$-DIMETHYLBENZYL)-PHENYL]-2H-BENZOTRIAZOLE AND STABILIZED COMPOSITIONS

[75] Inventors: Martin Dexter, Briarcliff Manor; Roland A. E. Winter, Armonk, both of N.Y.

[73] Assignee: Ciba-Geigy Corporation, Ardsley, N.Y.

[21] Appl. No.: 918,984

[22] Filed: Jun. 26, 1978

[51] Int. Cl.$^2$ .................. C08K 5/34; C07D 249/20
[52] U.S. Cl. .................. 260/45.8 N; 260/206; 548/257
[58] Field of Search .................. 260/308 R, 45.8 N

[56] References Cited

U.S. PATENT DOCUMENTS

| | | | |
|---|---|---|---|
| 3,004,896 | 10/1961 | Heller | 167/90 |
| 3,055,896 | 9/1962 | Boyle | 260/249.5 |
| 3,072,585 | 1/1963 | Milliones | 260/22 |
| 3,189,615 | 6/1965 | Heller | 260/308 |
| 3,230,194 | 1/1966 | Boyle | 260/45.8 |
| 4,041,044 | 9/1977 | White | 260/308 B |
| 4,127,501 | 11/1978 | Wang | 252/403 |

FOREIGN PATENT DOCUMENTS 53-158588  5/1978  Japan .

OTHER PUBLICATIONS

Chemical Abstracts: vol. 84, 136662j, Koga.

*Primary Examiner*—Donald G. Daus
*Assistant Examiner*—Lisa Jones
*Attorney, Agent, or Firm*—Luther A. R. Hall

[57] ABSTRACT

2-[2-Hydroxy-3,5-di-($\alpha,\alpha$-dimethylbenzyl)phenyl]-2H-benzotriazole exhibits outstanding efficacy in protecting organic substrates from light-induced deterioration as well as good resistance to loss by volatilization or exudation during the high temperature processing of stabilized compositions.

10 Claims, No Drawings

2-[2-HYDROXY-3,5-DI-(α,α-DIMETHYLBENZYL)-PHENYL]-2H-BENZOTRIAZOLE AND STABILIZED COMPOSITIONS

BACKGROUND OF THE INVENTION

The present invention relates to selected 2-aryl-2H-benzotriazoles which are useful in protecting light-sensitive organic materials from deterioration and to stabilized compositions containing said benzotriazoles.

The UV-absorber of the o-hydroxyphenyl-2H-benzotriazole class have long been known as effective light stabilizers for organic materials and have enjoyed considerable commercial success.

The description, preparation and uses of these valuable 2-aryl-2H-benzotriazoles are further taught in U.S. Pat. Nos. 3,004,896; 3,055,896; 3,072,585; 3,074,910; 3,189,615 and 3,230,194.

However the hitherto known 2-aryl-2H-benzotriazoles of this group have in some circumstances exhibited limited compatibility in certain substrates, and excessive tendency to exude, sublime and/or volatilize during processing of stabilized compositions into sheets, films, fibers or other pellicles when processing must be done at elevated temperatures. Likewise such benzotriazoles may also suffer undue loss by volatilization or sublimation from fabricated structures, particularly thin films or coatings, especially when subjected to elevated temperatures during use.

Attempts have been made to increase compatibility and to reduce volatilization loss by modifying the structure of the benzotriazoles.

In U.S. Pat. No. 3,230,194, a higher alkyl group was substituted for methyl and the compound 2-(2-hydroxy-5-tert-octylphenyl)-2H-benzotriazole exhibited superior compatibility and performance in polyethylene.

In U.S. Pat. No. 4,127,586, still other modifications to the 2-aryl-2H-benzotriazole moiety were made to increase still further compatibility in substrates and resistance to volatilization. The compound 2-[2-hydroxy-3-(1-phenylethyl)-5-methylphenyl]-2H-benzotriazole described therein exhibited better compatibility and better resistance to loss by volatilization during processing than did the earlier prior art benzotriazole compounds.

In Japanese Kokai 158588/75, other benzotriazole light stabilizers such as 2-(2-hydroxy-3-α,α-dimethylbenzyl-5-methylphenyl)-2H-benzotriazole are disclosed.

However, still better resistance to loss from stabilized compositions during high temperature processing remained a practical objective and need in the art for the benzotriazole UV-absorbers.

The instant compounds such as 2-[2-hydroxy-3,5-di-(α,α-dimethylbenzyl)phenyl]-2H-benzotriazole exhibit surprisingly superior resistance to loss from stabilized compositions during high temperature processing or in end use applications where coatings or films of the stabilized compositions are exposed even to ambient weathering and light exposures compared to stabilized compositions containing the 2-aryl-2H-benzotriazoles of the prior art.

In U.S. Pat. No. 4,041,044 an improved process for making 2-aryl-2H-benzotriazoles is taught. In the broadest generic scope in said reference, 2-[2-hydroxy-3,5-di-(α,α-dimethylbenzyl)phenyl]-2H-benzotriazole and 5-chloro-2-[2-hydroxy-3,5-di-(α,α-dimethylbenzyl)phenyl]-2H-benzotriazole are disclosed. Neither compound was exemplified nor prepared in said reference and the outstanding properties of these compounds now seen compared to other prior art benzotriazoles were not then recognized from the myriad of possible compounds generically disclosed in this reference.

DETAILED DISCLOSURE

This invention pertains to selected 2-aryl-2H-benzotriazole light absorbers and to organic materials, both polymeric and non-polymeric, stabilized thereby.

More particularly, the 2-aryl-2H-benzotriazoles of this invention are represented by the Formula I

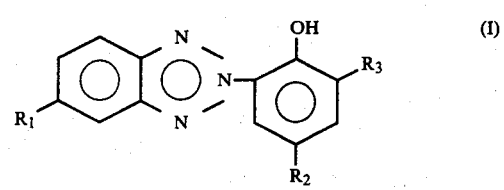

wherein $R_1$ is hydrogen or chloro, $R_2$ and $R_3$ are independently the group

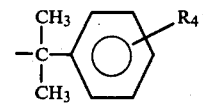

where $R_4$ is hydrogen or lower alkyl.

When $R_4$ is lower alkyl, the alkyl group is in the meta or para position, usually the para position. Typical lower alkyl groups are methyl, ethyl, isopropyl, tert-butyl, tert-amyl and sec-hexyl.

Preferably the instant compounds are those where $R_2$ and $R_3$ are the same and $R_4$ is hydrogen or p-methyl.

Most preferably $R_4$ is hydrogen.

Particularly preferred is the compound 2-[2-hydroxy-3,5-di-(α,α-dimethylbenzyl)phenyl]-2H-benzotriazole.

SYNTHESIS OF COMPOUNDS

The compounds of this invention are made by the following procedure:

Step I:

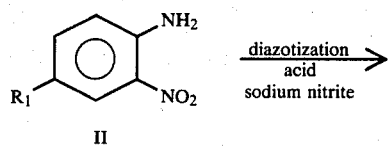

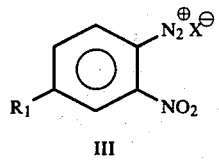

X is an anion such as chloride or sulfate.

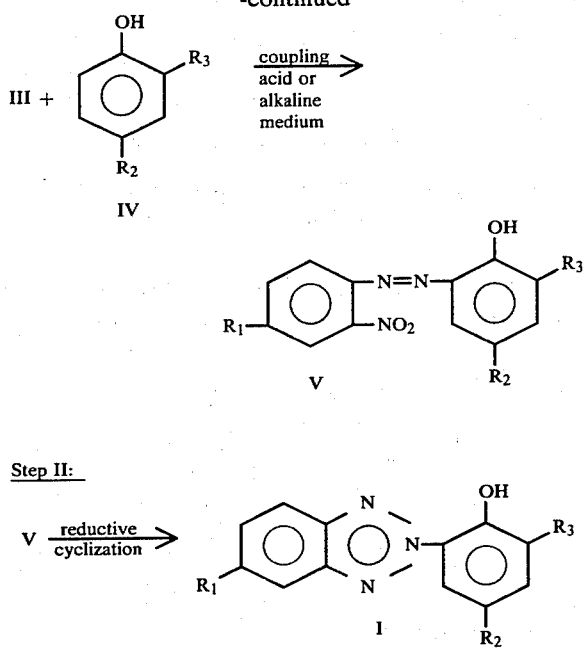

$R_1$, $R_2$ and $R_3$ are as described earlier in the specification.

Step I is the coupling of a diazonium compound with a phenol and can be carried out under either acid or alkaline conditions. When the coupling of the phenols bearing an aralkyl group in one ortho position to the hydroxyl moiety is carried out in acid medium, the yields of coupled product, the o-nitroazobenzene intermediate (V), are generally under 50% of theory.

Surprisingly when the same coupling reaction is carried out in strongly alkaline medium (pH over 10), the diazonium solution does not decompose to form nitrogen, but couples with facility to the phenol giving high yields (over 80% of theory) of the intermediate (V).

Step II involves the reductive cyclization of the intermediate V to the corresponding 2-aryl-2H-benzotriazole. This can be conveniently carried out by a number of known reduction methods including zinc and alkali, hydrazine, and catalytic hydrogenation with noble metal or nickel catalysts for this reaction. Good yields of the 2-aryl-2H-benzotriazoles are obtained by using such systems.

The various starting materials, i.e., phenols, o-nitroaniline, 5-chloro-2-nitroaniline, α-methylstyrene, are largely available as items of commerce or can easily be prepared by known methods.

The compounds of this invention are effective light stabilizers in a wide range of organic polymers. Polymers which can be stabilized include:

1. Polymers which are derived from mono- or diolefins, e.g., polyethylene which can optionally be cross-linked, polypropylene, polyisobutylene, polymethylbutene-1, polymethylpentene-1, polyisoprene, polybutadiene.
2. Mixtures of the homopolymers cited under (1), for example mixtures of polypropylene and polyethylene, polypropylene and polybutene-1, polypropylene and polyisobutylene.
3. Copolymers of the monomers based on the homopolymers cited under (1), for example ethylene/propylene copolymers, propylene/butene-1 copolymers, propylene/isobutylene copolymers, ethylene/butene-1 copolymers as well as terpolymers of ethylene and propylene with a diene, for example hexadiene, dicyclopentadiene or ethylidene norbornene, and copolymers of α-olefins, e.g., ethylene with acrylic or methacrylic acid.
4. Polystyrene.
5. Copolymers of styrene and of α-methylstyrene, for example styrene/butadiene copolymers, styrene/acrylonitrile copolymers, styrene/acrylonitrile/methacrylate copolymers, styrene/acrylonitrile copolymers modified with acrylic ester polymers to provide impact strength as well as block copolymers, e.g., styrene/butadiene/styrene block copolymers.
6. Graft copolymers of styrene, for example the graft polymer of styrene to polybutadiene, the graft polymer of styrene with acrylonitrile to polybutadiene as well as mixtures thereof with the copolymers cited under (5), commonly referred to as acrylonitrile/butadiene/styrene or ABS plastics.
7. Halogen-containing vinyl polymers, for example polyvinyl chloride, polyvinylidene chloride, polyvinyl fluoride, polychloroprene, chlorinated rubbers, vinyl chloride/vinylidene chloride copolymers, vinyl chloride/vinyl acetate copolymers, vinylidene chloride/vinyl acetate copolymers.
8. Polymers which are derived from α,β-unsaturated acids and derivatives thereof, polyacrylates and polymethacrylates, polyacrylic amides and polyacrylonitrile. The instant compounds are advantageously used in heat-curable acrylic resin lacquers which are composed of a copolymer of acrylic acid and one or more of its derivatives, and a melamine-formaldehyde resin.
9. Polymers which are derived from unsaturated alcohols and amines and from the acyl derivatives thereof or acetals, for example polyvinyl alcohol, polyvinyl acetate, polyvinyl stearate, polyvinyl benzoate, polyvinyl maleate, polyvinyl butyral, polyallyl phthalate, polyallyl melamine and copolymers thereof with other vinyl compounds, for example ethylene/vinyl acetate copolymers.
10. Homopolymers and copolymers which are derived from epoxides, for example polyethylene oxide or the polymers which are derived from bis-glycidyl ethers.
11. Polyacetals, for example polyoxymethylene, as well as polyoxymethylenes which contain ethylene oxide as comonomer.
12. Polyalkylene oxides, for example polyoxyethylene, polypropylene oxide or polyisobutylene oxide.
13. Polyphenylene oxides.
14. Polyurethanes and polyureas, such as in urethane coatings.
15. Polycarbonates.
16. Polysulfones.
17. Polyamides and copolyamides which are derived from diamines and dicarboxylic acids and/or from aminocarboxylic acids or the corresponding lactams, for example polyamide 6, polyamide 6/6, polyamide 6/10, polyamide 11, polyamide 12, poly-m-phenyleneisophthalamide.
18. Polyesters which are derived from dicarboxylic acids and dialcohols and/or from hydroxycarboxylic acids or the corresponding lactones, for example polyethylene glycol terephthalate, poly-1,4-dimethylolcyclohexane terephthalate.

19. Cross-linked polymers which are derived from aldehydes on the one hand and from phenols, ureas and melamine on the other, for example phenol/formaldehyde, urea/formaldehyde and melamine/formaldehyde resins.

20. Alkyd resins, for example glycerol/phthalic acid resins and mixtures thereof with melamine/formaldehyde resins.

21. Unsaturated polyesters resins which are derived from copolyesters of saturated and unsaturated dicarboxylic acids with polyhydric alcohols as well as from vinyl compounds as cross-linking agents and also the halogen-containing, flame-resistant modifications thereof.

22. Natural polymers, for example cellulose, rubber, as well as the chemically modified homologous derivatives thereof, for example cellulose acetates, cellulose propionates and cellulose butyrates and the cellulose ethers, for example methyl cellulose.

While compounds of this invention are very effective stabilizers for a host of organic substrates subject to light induced deterioration, as are the 2-aryl-2H-benzotriazole light absorbers in general, the instant compounds with their surprising resistance to loss from a stabilized composition during high temperature processing due to volatilization, exudation or sublimation have particular value in stabilizing polymeric substrates which are perforce processed at elevated temperatures.

Thus, the compounds of this invention are particularly useful as stabilizers for the protection of polyesters, for instance poly(ethylene terephthalate), poly(butylene terephthalate) or copolymers thereof; of polycarbonates, for example polycarbonate derived from bisphenol A and phosgene, or copolymers thereof; of polysulfones; of polyamides such as nylon-6, nylon-6,6, nylon 6,10 and the like as well as copolyamides; of thermoset acrylic resins; of thermoplastic acrylic resins; of polyolefins such as polyethylene, polypropylene, copolyolefins and the like; and of any polymer system requiring high temperature processing and fabrication.

Although the compounds of the invention may be used above to provide a light stabilizing function, the compounds of this invention are often combined with other stabilizers, even other light stabilizers, in the preparation of stabilized compositions. The stabilizers may be used with phenolic antioxidants, pigments, colorants or dyes, light stabilizers such as hindered amines, metal deactivators, etc.

In general, the stabilizers of this invention are employed from about 0.1 to about 5% by weight of the stabilized composition, although this will vary with the particular substrate and application. An advantageous range is from about 0.5 to about 3%.

The stabilizers of Formula I may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain from about 0.1 to about 5%, preferably from about 0.5 to about 3% by weight of various conventional additives, such as the following, particularly phenolic antioxidants or light-stabilizers, or mixtures thereof:

1. Antioxidants 1.1 Simple 2,6-dialkylphenols, such as, for example, 2,6-di-tert.-butyl-4-methylphenol, 2-tert.-butyl-4,6-dimethylphenol, 2,6-di-tert.-butyl-4-methoxymethylphenol and 2,6-dioctadecyl-4-methylphenol.

1.2 Derivatives of alkylated hydroquinones, such as for example, 2,5-di-tert.-butyl-hydroquinone, 2,5-di-tert.-amylhydroquinone, 2,6-di-tert.-butyl-hydroquinone, 2,5-di-tert.-butyl-4-hydroxy-anisole, 3,5-di-tert.-butyl-4-hydroxy-anisole, 3,5-di-tert.-butyl-4-hydroxyphenyl stearate and bis-(3,5-di-tert.-butyl-4-hydroxyphenyl) adipate.

1.3 Hydroxylated thiodiphenyl ethers, such as for example, 2,2'-thio-bis-(6-tert.-butyl-4-methylphenol), 2,2'-thio-bis-(4-octylphenol), 4,4'-thio-bis-(6-tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxyphenyl) disulfide.

1.4 Alkylidene-bisphenols, such as, for example, 2,2'-methylene-bis-(6-tert.-butyl-4-methylphenol), 2,2'-methylene-bis-(6-tert.-butyl-4-ethylphenol), 4,4'-methylene-bis-(6-tert.-butyl-2-methylphenol, 4,4'-methylene-bis-(2,6-di-tert.-butylphenol), 2,6-di(3-tert.-butyl-5-methyl-2-hydroxybenzyl)-4-methylphenol, 2,2'-methylene-bis-[4-methyl-6-(α-methylcyclohexyl)-phenol], 1,1-bis(3,5-dimethyl-2-hydroxyphenyl)-butane, 1,1-bis-(5-tert.-butyl-4-hydroxy-2-methylphenyl)-butane, 2,2-bis-(3,5-di-tert.-butyl-4-hydroxyphenyl)-propane, 1,1,3-tris-(5-tert.-butyl-4-hydroxy-2-methylphenyl)-butane, 2,2-bis-(5-tert.-butyl-4-hydroxy-2-methylphenyl)-4-n-dodecylmercaptobutane, 1,1,5,5-tetra-(5-tert.-butyl-4-hydroxy-2-methylphenyl)-pentane and ethylene glycol bis-[3,3-bis-(3-tert.-butyl-4-hydroxyphenyl)-butyrate].

1.5 O-, N- and S-benzyl compounds, such as for example, 3,5,3',5'-tetra-tert.-butyl-4,4'-dihydroxydibenzyl ether, octadecyl 4-hydroxy-3,5-dimethylbenzyl-mercaptoacetate, tris-(3,5-di-tert.-butyl-4-hydroxybenzyl)-amine and bis-(4-tert.-butyl-3-hydroxy-2,6-dimethylbenzyl) dithioterephthalate.

1.6 Hydroxybenzylated malonates, such as for example, dioctadecyl 2,2-bis-(3,5-di-tert.-butyl-2-hydroxybenzyl)-malonate, dioctadecyl 2-(3-tert.-butyl-4-hydroxy-5-methylbenzyl)-malonate, di-dodecylmercapto-ethyl 2,2-bis-(3,5-di-tert.-butyl-4-hydroxybenzyl)-malonate and di-[4-(1,1,3,3-tetramethylbutyl)-phenyl] 2,2-bis-(3,5-di-tert.-butyl-4-hydroxybenzyl)-malonate.

1.7 Hydroxybenzyl-aromatic compounds, such as, for example, 1,3,5-tri-(3,5-di-tert.-butyl-4-hydroxybenzyl)-2,4,6-trimethylbenzene, 1,4-di-(3,5-di-tert-butyl-4-hydroxybenzyl)-2,3,5,6-tetramethylbenzene and 2,4,6-tri-(3,5-di-tert.-butyl-4-hydroxybenzyl)-phenol.

1.8 s-Triazine compounds, such as for example 2,4-bis-octylmercapto-6-(3,5-di-tert.-butyl-4-hydroxyanilino)-s-triazine, 2-octylmercapto-4,6-bis-(3,5-di-tert.butyl-4-hydroxy anilino)-s-triazine, 2-octylmercapto-4,6-bis-(3,5-di-tert.-butyl-4-hydroxyphenoxy)-s-triazine, 2,4,6-tris-(3,5-di-tert.-butyl-4-hydroxyphenoxy)-s-triazine, 2,4,6-tris-(3,5-di-tert-butyl-4-hydroxyphenylethyl)-s-triazine and 1,3,5-tris-(3,5-di-tert.-butyl-4-hydroxybenzyl)isocyanurate.

1.9 Amides of β-(3,5-di-tert.-butyl-4-hydroxyphenyl)-propionic acid, such as, for example, 1,3,5-tris-(3,5-di-tert.-butyl-4-hydroxyphenyl-propionyl)-hexahydro-s-triazine and N,N'-di-3,5-di-tert.-butyl-4-hydroxyphenyl-propionyl)-hexamethylenediamine, N,N'-bis-β-(3,5-di-t-butyl-4-hydroxyphenyl)-propionyl-hydrazine.

1.10 Esters of β-(3,5-di-tert.-butyl-4-hydroxyphenyl)-propionic acid with monohydric or polyhydric alcohols, such as for example, with methanol, ethanol, octadecanol, 1,6-hexanediol, 1.9-nonanediol, ethylene glycol, 1,2-propanediol, diethylene glycol, thiodiethylene glycol, neopentylglycol, pentaerythritol, 3-thiaundecanol, 3-thia-pentadecanol, trimethylhexnediol, trimethylolethane, trimethylolpropane, tris-hydroxyethyl isocyanurate and 4-hydroxymethyl-1-phospha-2,6,7-trioxabicyclo-[2.2.2]octane.

1.11 Esters of β-(5-tert.-butyl-4-hydroxy-3-methylphenylpropionic acid with monohydric or polyhydric alcohols, such as for example, with methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thiaundecanol, 3-thia-pentadecanol, trimethylhexanediol, trimethylolethane, trimethylolpropane, tri-hydroxyethyl isocyanurate and 4-hydroxymethyl-1-phospha-2,6,7-trioxabicyclo[2.2.2]octane.

1.12 Esters of 3,5-di-tert.-butyl-4-hydroxyphenylacetic acid with monohydric or polyhydric alcohols, such as for example, with methanol, ethanol, octadecanol, 1,6-hexandiol, 1,9-nonanediol, ethylene glycol, 1,2-propenediol, diethylene glycol, thio-diethylene glycol, neopentylglycol, pentaerythritol, 3-thiaundecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2.2.2]-octane especially the tetrakis ester of pentaerythritol.

1.13 Benzylphosphonates, such as, for example, dimethyl 3,5 di-tert.-butyl-4-hydroxybenzylphosphonate, diethyl 3,5-di-tert.-butyl-4-hydroxybenzylphosphonate, dioctadecyl 3,5-di-tert.-butyl-4-hydroxybenzylphosphonate and dioctadecyl 5-tert.-butyl-4-hydroxy-3-methylbenzylphosphonate.

2. Light-stabilizers 2.1 Esters of optionally substituted benzoic acids, e.g., 3,5-di-tert.-butyl-4-hydroxybenzoic acid, 2,4-di-tert.-butylphenyl ester or -octadecyl ester or 2-methyl-4,6-di-tert.-butylphenyl ester.

2.2 Sterically hindered amines, e.g., 4-benzoyl-2,2,6,6-tetramethylpiperidine, 4-stearyloxy-2,2,6,6-tetramethylpiperidine, bis-(2,2,6,6-tetramethylpiperidyl) sebacate, bis-(1,2,2,6,6-pentamethylpiperidyl) 2-n-butyl-2-(2-hydroxy-3,5-di-tert-butylbenzyl)malonate or 3-n-octyl-7,7,9,9-trimethyl-1,3,8-triazaspiro[4.5]decane-2,4-dione.

2.3 Oxalic acid diamides, e.g., 4,4'-di-octyloxy-oxanilide, 2,2'-di-octyloxy-5,5'-di-tert.-butyl-oxanilide, 2,2'-di-dode-cyloxy-5,5'-di-tert.-butyl-oxanilide, 2-ethoxy-2'-ethyl-oxanilide, N,N'-bis-(3-dimethyl-aminopropyl)-oxalamide, 2-ethoxy-5-tert.-butyl-2'-ethyl-oxanilide and the mixture thereof with 2-ethoxy-2'-ethyl-5,4'-di-tert.-butyl-oxanilide, or mixtures of ortho- and para-methoxy- as well as of o- and p-ethoxy-disubstituted oxanilides.

3. Metal deactivators, e.g., oxanilide, isophthalic acid dihydrazide, sebacic acid-bis-phenylhydrazide, bis-benzylideneoxalic acid dihydrazide, N,N'-diacetal-adipic acid dihydrazide, N,N'-bis-salicyloyl-oxalic acid dihydrazide, N,N'-bis-salicyloylhydrazine, N,N'-bis-(3,5-di-tert.-butyl-4-hydroxyphenylpropionyl)-hydrazine, N-salicyloyl-N'-salicylalhydrazine, 3-salicyloyl-amino-1,2-4-triazole or N,N'-bis-salicyloyl-thiopropionic acid dihydrazide.

4. Basic co-stabilizers, e.g., alkali metal salts and alkaline-earth metal salts of higher fatty acids, for example Ca-stearate, Zn-stearate, Mg-behenate, Na-ricinoleate or K-palmitate.

5. Nucleation agents, e.g., 4-tert.-butylbenzoic acid, adipic acid or diphenylacetic acid.

6. Phosphites and phosphonites, such as, for example, triphenyl phosphite, diphenylalkyl phosphites, phenyldialkyl phosphites, tri-(nonyl-phenyl) phosphite, trilauryl phosphite, trioctadecyl phosphite and 3,9-isodecyloxy-2,4,8,10-tetraoxa-3,9-diphospha-[5.5]-undecane and tetra(2,4-di-tert-butylphenyl) diphenylene-4,4'-bis(phosphonite).

Other additives that can be incorporated in the stabilized compositions are thiosynergists such as dilauryl thiodipropionate, lubricants such as stearyl alcohol, fillers, asbestos, kaolin, talc, glass fibers, pigments, optical brighteners, flameproofing agents and antistatic agents.

The following examples are presented for the purpose of illustration only and are not to be construed to limit the nature or scope of the instant invention in any manner whatsoever.

EXAMPLE 1

2,4-Di-(α,α-dimethylbenzyl)phenol

This intermediate was made by the general procedure of U.S. Pat. No. 2,714,120 by reacting a mixture of 705.8 grams (7.5 moles) of phenol with 1772.7 grams (15 moles) of α-methylstyrene in the presence of 25.7 grams (0.135 moles) of p-toluenesulfonic acid monohydrate catalyst. This mixture was heated under nitrogen at 140° C. for 2.5 hours. The reaction mixture was cooled to 110° C. and 1125 ml of toluene was added. After washing the resulting solution at 80° C. with 750 ml of an aqueous solution of 37.5 grams of sodium carbonate and 75 grams of sodium chloride, the organic phase was washed thrice with 1000 ml of aqueous sodium chloride solution; then dried over anhydrous sodium sulfate; filtered and vacuum distilled. The above-named product was obtained as the main fraction boiling at 172°–175° C./0.15–0.18 mm Hg in a yield of 1229.8 grams (49.6% of theory). The product melted 63°–65° C.

EXAMPLE 2

2-Nitro-2'-hydroxy-3',5'-di(α,α-dimethylbenzyl)azobenzene

Acid Coupling Process

To a 2-liter, 3-necked flask fitted with a stirrer and thermometer was charged 90.6 grams of a 26% aqueous solution of technical naphthalenesulfonic acid, 1.9 grams of Triton X-207 (non-ionic surfactant), 5.6 grams of Conco AAS-90F (sodium dodecylbenzenesulfonate) and 90 ml of water. The mixture was warmed to 40° C. and then 116.5 grams of 2,4-di(α,α-dimethylbenzyl)-phenol, preheated to 90° C., was slowly added to the mixture with vigorous stirring keeping the temperature at 40° C.

A cold solution of o-nitro benzene diazonium chloride, prepared from 49.8 grams (0.36 mole) of o-nitroaniline and 24.9 grams (0.36 mole) of sodium nitrite in concentrated aqueous hydrochloric acid solution at a temperature of −5° to 0° C., was added dropwise into the reaction mixture over a 3-hour period. The resulting deep red to black reaction mixture was kept at 40° C. overnight. The temperature was raised to 65° C. for 1 hour; then the 95° C. for another 30 minutes. After cooling to 85° C., the reaction mixture was isolated as a resinous, viscous, deep red-black mass by filtration.

The crude product was triturated with four 200 ml portions of hot (75° C.) water; then with 400 ml of methanol overnight; and stirred in a blender with another 400 ml of methanol to yield a fine granular product. The dark red o-nitroazobenzene intermediate named above was obtained in a yield of 81.9 grams (48.4% of theory) and melted at 139°–141° C. Thin layer chromatography indicated a homogeneous product with an $R_f$ value of 0.61 on silicagel (3 cyclohexane: 1 ethyl acetate).

EXAMPLE 3

2-[2-Hydroxy-3,5-di-($\alpha,\alpha$-dimethylbenzyl)phenyl]-2H-benzotriazole

To a 5-liter 3-necked flask fitted with a stirrer, thermometer, reflux condenser and nitrogen inlet was charged 386 grams (0.805 mol) of the o-nitroazobenzene intermediate of Example 2 and 1200 ml of toluene. To the resulting solution was added 240 ml of isopropanol and 240 ml of water. A nitrogen atmosphere was imposed and 160 ml of 50.1% aqueous sodium hydroxide was added. A flask containing 158.2 gram (2.42 gram-atoms) of zinc was connected to the reaction flask by Gooch rubber tubing and the zinc dust was added portionwise to the reaction mixture over a 90-minute period. The zinc was added at such a rate to keep the internal temperature between 40° and 45° C. After the zinc was all added, the reaction mixture was heated for 1 hour at 40° C. and then for 3 hours at 70° C. The mixture was cooled to room temperature and acidified with 600 ml of concentrated hydrochloric acid.

The zinc sludge was removed by filtration. The product was contained in the organic layer, which was washed with four 340 ml portions of dilute hydrochloric acid, and then dried over anhydrous sodium sulfate. The organic solvent was removed in vacuo to yield a crude product as a viscous syrup which crystallized on standing.

The crude product was recrystallized first from 750 ml of ethyl acetate to give 225 grams (62.5% of theory) of light tan crystals. The product was further purified by recrystallization from 1000 ml of a 4:1 mixture of acetonitrile:ethyl acetate and then dissolved in 1250 ml of toluene. The toluene solution was extracted with 70% aqueous sulfuric acid to remove colored impurities before yielding 219.3 grams (60.9% theory) of slightly off white crystals melting at 140°–141° C. of the above named compound. (Compound 1).

Analysis: Calcd for $C_{30}H_{29}N_3O$: C: 80.51; H, 6.53; N: 9.39. Found C: 80.53; H, 6.54; N: 9.51.

EXAMPLE 4

2-Nitro-2'-hydroxy-3',5'-di($\alpha,\alpha$-dimethylbenzyl)azobenzene

Alkaline Coupling Process

To a 500-ml 3-necked flask fitted with a stirrer, thermometer, pressure equalized addition funnel and nitrogen inlets and outlets were charged 13.5 grams (0.21 mole) of potassium hydroxide pellets and 10 ml of water. The resulting hot solution was diluted with 80 ml of methanol. After flushing with nitrogen, 16.5 grams (0.05 mole) of 2,4-di-($\alpha,\alpha$-dimethylbenzyl)phenol and 85 ml of methanol were added to give a clear solution which was then cooled to −4° C. A cold solution of o-nitrobenzene diazonium chloride in concentrated hydrochloric acid solution (42.9 grams=0.06 mole of diazonium solution) was added over a period of 15 minutes with rapid stirring while keeping the temperature between −2° and 0° C. The deep purple color of the azodye-phenoxide developed instantaneously as the diazonium solution was added. The resulting mixture was stirred for another 10 minutes at −1° to 1° C. The suspension was then acidified with 20 ml of glacial acetic acid over a 2-minute period at 1° to 3° C. The resulting brick red suspension was stirred for 15 minutes as the temperature was allowed to rise to ambient temperature and then filtered. The filter cake was washed with a cold solution of 40 grams ice in 160 ml of methanol and then with 1800 ml of water.

The bright red crude product was vacuum dried at 60° C. at 75 mm Hg for 16 hours yielding 22.7 grams of material melting at 135°–140° C. Spectrophotometric assay indicated 86.7% purity giving a calculated yield of pure compound of 82% of theory.

The crude product was conveniently recrystallized from hot n-butanol using 5 ml per gram to give 95% recovery of pure product melting at 147°–148° C.

EXAMPLE 5

2-[2-Hydroxy-3,5-di-($\alpha,\alpha$-dimethylbenzyl)phenyl]-2H-benzotriazole

When in following the general procedure of Example 3 an equivalent amount of 2-nitro-2'-hydroxy-3',5'-di($\alpha,\alpha$-dimethylbenzyl)azobenzene prepared Example 4 was substituted for that prepared in Example 2, the above-named product was obtained in a yield of 80.2% of theory as very pale yellowish crystals melting at 139.5°–140° C. (Compound 1).

Analysis: Calcd for $C_{30}H_{29}N_3O$: C: 80.51; H, 6.53; N: 9.39. Found C: 80.47; H, 6.28; N: 9.40.

EXAMPLES 6–8

Alkaline Coupling Process

When the alkaline coupling procedure of Example 4 was used with o-nitrobenzene diazonium chloride and a variety of phenols other than 2,4-di($\alpha,\alpha$-dimethylbenzyl)phenol, the yields of the corresponding o-nitroazobenzene products varied widely depending on the substitution in the phenol being coupled.

| Example | Phenol | Yield (%) of Corresponding o-nitroazobenzene |
|---|---|---|
| 6 | 2,4-di-tert-amyl | poor* |
| 7 | 2,4-di-tert-octyl | poor* |
| 4 | 2,4-di($\alpha,\alpha$-dimethylbenzyl) | 86.7 |
| 8 | 2-(1-phenylethyl)-4-methyl | 84.3 |

*Some 30 to 60% of the diazonium solution decomposed with nitrogen evolution resulting in poor yields of any coupled product.

EXAMPLE 9

4-Chloro-2-nitro-2'-hydroxy-3',5'-di($\alpha,\alpha$-dimethylbenzyl)azobenzene

When, using the general procedure of Example 2, an equivalent amount of the diazonium solution prepared from 4-chloro-2-nitroaniline was substituted for the diazonium solution prepared from 2-nitroaniline, the above-named compound was prepared in a yield of 47.3% as a very dark red solid.

EXAMPLE 10

5-Chloro-2-[-2'-hydroxy-3',5'-di($\alpha,\alpha$-dimethylbenzyl)-phenyl]-2H-benzotriazole When, using the general procedure of example 3, the amount of 4-chloro-2-nitro-2'-hydroxy-3',5'-di-($\alpha,\alpha$-dimethylbenzyl)azobenzene was substituted for 2-nitro-2'-hydroxy-3',5'-di-($\alpha,\alpha$-dimethylbenzyl)azobenzene, the above-named compound was prepared in a yield of 70.0% as light tan crystalls melting at 160°–161° C.

Analysis: Calcd for $C_{30}H_{28}ClN_3O$: C: 74.45; H, 5.86; N: 8.72. Found C: 74.53; H, 6.11; N: 8.72.

EXAMPLE 11

Resistance to Loss of Benzotriazole Stabilizers

A number of 2-aryl-2H-benzotriazole light stabilizers were subjected to thermal gravimetric analysis both isothermally at 280° C. to indicate the time in minutes to reach 10%, 50% and 100% weight loss of the stabilizer as well as in a scanning mode at a heating rate of 10° (C.) per minute to ascertain the temperature at which 10% and 50% weight loss of stabilizer were observed.

Experimental data are given on Table A.

These results correlate closely with the resistance of the indicated stabilizer to exudation or volatilization during any processing step with polymer formulations during the preparation of sheet, film, fiber or other fabricated pellicles. The absence or essential absence of exuded or volatilized stabilizer on processing equipment (i.e., rollers, guides, orifices, and the like) and increases significantly the times between required shut-downs of continuously operated process equipment and represents enormous practical and economic savings related to the specific stabilizer used.

TABLE A

| | TGA Data | | | | |
|---|---|---|---|---|---|
| | Isothermal at 280° C. Time (minutes) to Indicated Weight Loss of Stabilizer | | | Scanning (at 10° (C.) per minute Temperature °C. to Indicated Weight Loss of Stabilizer | |
| Stabilizer* | 10% | 50% | 100% | 10% | 50% |
| TINUVIN P | 0.4 | 0.75 | 1.2 | 182 | 215 |
| TINUVIN 350 | 0.6 | 1.0 | 1.8 | 210 | 247 |
| CYASORB UV-5411 | 0.6 | 1.9 | 3.5 | 225 | 260 |
| Compound 333 | 0.8 | 3.0 | 6.0 | 250 | 290 |
| Compound 1 | 6.0 | 24.0 | 56.0 | 300 | 340 |

*TINUVIN P is 2-(2-hydroxy-5-methylphenyl)-2H-benzotriazole.
TINUVIN 350 is 2-(2-hydroxy-3-tert-butyl-5-sec-butylphenyl)-2H-benzotriazole.
CYASORB UV-5411 is 2-(2-hydroxy-5-tert-octylphenyl)-2H-benzotriazole.
Compound 333 is 2-[2-hydroxy-3-(1-phenylethyl)-5-methylphenyl]-2H-benzotriazole.

Compound 1 (Example 3 and 5) clearly exhibits much greater resistance to sublimation and exudation (much less volatility) than the prior art benzotriazole stabilizers. Compound 1 incorporated in a stabilized polymer composition would remain there during processing permitting excellent processability coupled with a final polymer pellicle with greater protection against subsequent light-induced deterioration.

EXAMPLE 12

Retention of Benzotriazole Stabilizers in Polycarbonate During Sheet Production Polycarbonate (Lexan, General Electric) resin was formulated with 0.3% by weight of a number of 2-aryl-2H-benzotriazole light absorber stabilizers. The formulated resin was extruded at 600° F. (316° C.) into thin sheets. The resultant sheets were dissolved in methylene chloride and the polycarbonate precipitated with methanol. The amount of benzotriazole stabilizer retained in the polycarbonate sheet after fabrication was determined by gas chromatographic analysis.

The results are given on Table B.

TABLE B

| Stabilizer* | % Retained in Polycarbonate Sheet after Fabrication |
|---|---|
| TINUVIN 350 | 82 |
| CYASORB UV-5411 | 87 |
| Compound 333 | 100 |
| Compound 1 | 100 |

*See Table A for chemical names of these stabilizers.

These data confirm the results on Table A that the instant Compound 1 resists sublimation or exudation during processing. Compound 333 likewise exhibits good volatility resistance in this test.

EXAMPLE 13

Resistance to Loss During Cure and Weathering of Benzotriazole Stabilizers in Thermoset Acrylic Coatings Several thermoset acrylic resin and an alkyd/acrylic resin systems were formulated with 2% by weight of several benzotriazole light absorber stabilizers and cast onto glass plates as 1$\mu$ thick coatings. The coatings were then cured by heating at elevated temperatures for selected periods of time. The loss of benzotriazole light stabilizer was then ascertained by UV-absorption analysis of the coatings. Any decrease in absorbance of the coatings can be correlated to loss of benzotriazole stabilizer during the curing step.

These cured coatings were also subjected to the accelerated (quick) weathering test (QUV) involving alternating 4-hour period of UV irradiation at 60° C. with a 4-hour period of condensation (rain) at 50° C. for each cycle for a total of 670 hours. Again any decrease in absorbance of the weathered coatings can be correlated to loss of the benzotriazole stabilizer during the curing and weathering period.

Results are given on Table C.

TABLE C

| | Absorbance Loss During Cure or Weathering (Percent) | | | | | | |
|---|---|---|---|---|---|---|---|
| | Thermoset Acrylic Resin Systems | | | | | Alkyd/Acrylic Resin | |
| | Single layer | | 2-Coat System | | High Solids | | |
| Stabilizer* | Heated 25 min at 120° C. | After Weathering | Heated 20 min at 135° C. | After Weathering | Heated 30 minutes at 150° C. | Heated 30 minutes at 125° C. | After Weathering |
| TINUVIN 328 | 25 | 35 | 59 | 69 | 95 | 77 | 100 |
| Compound 333 | 2 | 17 | 8 | 26 | 37 | 12 | 96 |

TABLE C-continued

| | Absorbance Loss During Cure or Weathering (Percent) | | | | | | |
|---|---|---|---|---|---|---|---|
| | Thermoset Acrylic Resin Systems | | | | | Alkyd/Acrylic Resin | |
| | Single layer | | 2-Coat System | | High Solids | | |
| Stabilizer* | Heated 25 min at 120° C. | After Weathering | Heated 20 min at 135° C. | After Weathering | Heated 30 minutes at 150° C. | Heated 30 minutes at 125° C. | After Weathering |
| Compound 1 | 0 | 5 | 0 | 10 | 0 | 0 | 73 |

*TINUVIN 328 is 2-(2-hydroxy-3,5-di-tert-amylphenyl)-2H-benzotriazole.
Compound 333 is 2-[2-hydroxy-3-(1-phenylethyl)-5-methylphenyl]-2H-benzotriazole.

As is seen from Table C, the instant compound exhibits far greater resistance to loss from the thermoset acrylic resin and alkyd/acrylic resin systems than do other benzotriazoles of the prior art. Compound 1 is discernibly less volatile than is Compound 333 of closely related structure.

EXAMPLE 14

Gloss Values of Acrylic Enamels and Lacquers Containing Benzotriazole Stabilizers after Weathering Several thermoset acrylic enamels and a thermoplastic acrylic lacquer were formulated to include a benzotriazole light absorber stabilizer. Gloss values were compared for the initial enamel or lacquer and after exposure to an accelerated weathering test (QUV where each cycle includes 4 hours of UV at 60° C. and 4 hours of condensation at 50° C.).

Results are given on Table D.

TABLE D

| | 20° Gloss Values of Enamels or Lacquers Containing Benzotriazole Stabilizers Before and After Weathering | | | | | |
|---|---|---|---|---|---|---|
| | Thermoset Acrylic Enamel A | | Thermoset Acrylic Enamel B | | Thermoplastic Acrylic Lacquer | |
| Stabilizer* | Initial | 800 hours QUV | Initial | 800 hours QUV | Initial | 200 hours QUV |
| No stabilizers | 65 | 15.4 | 67.3 | 25.1 | 77.8 | 23.1 |
| 1% TINUVIN 328 | 68.1 | 15.0 | 64.6 | 26.7 | — | — |
| 1% Compound 333 | 68.7 | 19.8 | 65.2 | 25.6 | 78.0 | 24.0 |
| 1% Compound 1 | 66.9 | 27.8 | 68.8 | 33.2 | 78.5 | 41.1 |
| 2% TINUVIN 328 | 64.8 | 16.6 | 59.2 | 23.1 | 77.1 | 33.5 |
| 2% Compound 333 | 68.6 | 19.4 | 63.5 | 30.3 | 77.4 | 41.0 |
| 2% Compound 1 | 66.7 | 27.2 | 69.3 | 39.0 | 79.1 | 41.0 |

*See Table C for chemical name of these stabilizers.

Formulations containing Compound 1 consistently gave better gloss values after QUV weathering than did those containing prior art benzotriazoles.

EXAMPLE 15

Stabilization of Polyethylene Terephthalate 0.5% of the compound of Example 3 is added as a stabilizer to molten polyethylene terephthalate at 270° C. with stirring under a nitrogen atmosphere. The resulting formulated polymer is ground with solid carbon dioxide.

The stabilized composition is extruded at elevated temperature into a film with little loss of stabilizer. The film is then exposed to actinic radiation. The stabilized film retains desirable physical properties for a longer period than does a film prepared from unstabilized polyester.

EXAMPLE 16

Stabilization of Polycarbonate

Polycarbonate (Lexan, General Electric) is mixed in a compounding extruder with 0.3% of the compound of Example 5. The stabilized composition is extruded into a sheet at elevated temperature with little loss of stabilizer. The sheet maintains physical properties after exposure to UV light for a longer period than does a sheet containing no stabilizer.

What is claimed is:

1. A compound of the formula

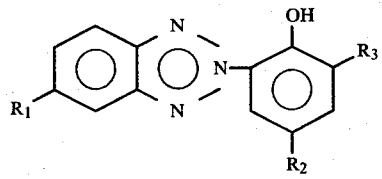

wherein
R₁ is hydrogen or chloro,
R₂ and R₃ are independently the group

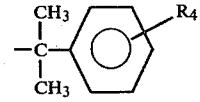

where R₄ is hydrogen or lower alkyl.

2. A compound according to claim 1 wherein R₁ is hydrogen or chloro, R₂ and R₃ are both the same and R₄ is hydrogen or p-methyl.

3. A compound according to claim 1 wherein R₄ is hydrogen.

4. A compound according to claim 1 which is 2-[2-hydroxy-3,5-di-(α,α-dimethylbenzyl)phenyl]-2H-benzotriazole.

5. A compound according to claim 1 which is 5-chloro-2-[2-hydroxy-3,5-di-(α,α-dimethylbenzyl)phenyl]-2H-benzotriazole.

6. A composition of matter comprising an organic material subject to light-induced deterioration stabilized with from 0.1 to 5% by weight of a compound according to claim 1.

7. A composition according to claim 6 wherein the organic material is a synthetic polymer.

8. A composition according to claim 7 wherein the polymer is selected from the group consisting of polyesters, polycarbonates, polysulfones, polyamides, thermoset acrylic resins, thermoplastic acrylic resins, polyolefins and polyurethanes.

9. A composition according to claim 8 stabilized with 2-[2-hydroxy-3,5-di($\alpha,\alpha$-dimethylbenzyl)phenyl]-2H-benzotriazole.

10. A composition according to claim 7 wherein the polymer is a thermoset acrylic resin or thermoplastic acrylic resin.

* * * * *